United States Patent
Suzuki et al.

(10) Patent No.: US 10,952,769 B2
(45) Date of Patent: Mar. 23, 2021

(54) MEDICAL RETRACTOR DEVICE

(71) Applicant: SUMITOMO BAKELITE CO., LTD., Shinagawa-ku (JP)

(72) Inventors: Zenetsu Suzuki, Akita (JP); Nobuyuki Kudo, Akita (JP)

(73) Assignee: SUMITOMO BAKELITE CO., LTD., Shinagawa-ku (JP)

(*) Notice: Subject to any disclaimer, the term of this patent is extended or adjusted under 35 U.S.C. 154(b) by 58 days.

(21) Appl. No.: 16/321,918

(22) PCT Filed: Aug. 4, 2017

(86) PCT No.: PCT/JP2017/028424
§ 371 (c)(1),
(2) Date: Jan. 30, 2019

(87) PCT Pub. No.: WO2018/026001
PCT Pub. Date: Feb. 8, 2018

(65) Prior Publication Data
US 2019/0175218 A1    Jun. 13, 2019

(30) Foreign Application Priority Data
Aug. 4, 2016 (JP) .............................. JP2016-153862

(51) Int. Cl.
*A61B 17/34* (2006.01)
*A61B 17/02* (2006.01)

(52) U.S. Cl.
CPC .......... *A61B 17/3423* (2013.01); *A61B 17/02* (2013.01); *A61B 17/34* (2013.01);
(Continued)

(58) Field of Classification Search
CPC . A61B 17/02; A61B 17/0218; A61B 17/0293; A61B 2017/0287; A61B 17/3423; A61B 17/3431
See application file for complete search history.

(56) References Cited

U.S. PATENT DOCUMENTS

| | | | | |
|---|---|---|---|---|
| 7,727,146 B2* | 6/2010 | Albrecht | ................ | A61B 17/02 600/208 |
| 7,736,306 B2* | 6/2010 | Brustad | .................. | A61B 17/02 600/208 |

(Continued)

FOREIGN PATENT DOCUMENTS

| JP | 5-76450 U | 10/1993 |
|---|---|---|
| JP | 2002-28163 A | 1/2002 |

(Continued)

OTHER PUBLICATIONS

International Search Report dated Oct. 3, 2017, in PCT/JP2017/028424, filed Aug. 4, 2017.

*Primary Examiner* — Anu Ramana
(74) *Attorney, Agent, or Firm* — Oblon, McClelland, Maier & Neustadt, L.L.P.

(57) ABSTRACT

A medical treatment implement which has an excellent degree of freedom of a procedure and into which a trocar can be re-stuck includes a tubular retractor main body configured to be indwelled in an incision wound and a converter (20) configured to close an opening end portion of an upper end of the retractor main body and to be puncturable with a trocar.

The converter (20) includes a ring-shaped frame portion (22) detachably mounted on the opening end portion and a sheet portion (21) which is mounted inside the frame portion (22) and airtightly covers the opening end portion. A compression force P is applied to the sheet portion (21) in an inner diameter direction.

20 Claims, 4 Drawing Sheets

(52) U.S. Cl.
CPC .... *A61B 17/3415* (2013.01); *A61B 2017/348* (2013.01); *A61B 2017/3433* (2013.01); *A61B 2017/3445* (2013.01)

(56) References Cited

U.S. PATENT DOCUMENTS

| | | | |
|---|---|---|---|
| 8,475,490 B2 | 7/2013 | Hess et al. | |
| 2004/0015185 A1* | 1/2004 | Ewers | A61B 17/3474 606/213 |
| 2004/0173218 A1 | 9/2004 | Yamada et al. | |
| 2007/0149859 A1* | 6/2007 | Albrecht | A61B 17/0218 600/208 |
| 2009/0187079 A1 | 7/2009 | Albrecht et al. | |
| 2010/0113882 A1 | 5/2010 | Widenhouse et al. | |

FOREIGN PATENT DOCUMENTS

| | | |
|---|---|---|
| JP | 2002-325769 A | 11/2002 |
| JP | 2012-215 A | 1/2012 |
| JP | 2012-196337 A | 10/2012 |
| JP | 5813849 B2 | 11/2015 |
| JP | 2016-512725 A | 5/2016 |
| WO | WO 2014/143656 A1 | 9/2014 |

\* cited by examiner

MEDICAL RETRACTOR DEVICE

CROSS-REFERENCE TO RELATED APPLICATIONS

This application is a national stage application of International Application No. PCT/JP2017/028424, filed Aug. 4, 2017, which is based upon and claims the benefit of priority to Japanese Patent Application No. 2016-153862, filed Aug. 4, 2016.

TECHNICAL FIELD

The present invention relates to a medical treatment implement that can be used and indwelled in an incision wound.

Priority is claimed on Japanese Patent Application No. 2016-153862, filed on Aug. 4, 2016, the content of which is incorporated herein by reference.

BACKGROUND OF THE INVENTION

In laparoscopic surgery, so-called single-hole surgery is performed in which surgery is performed by inserting a plurality of treatment tools such as forceps or optical devices from one incision wound. PTLs 1 and 2 disclose medical treatment implements called a retractor for inserting various treatment tools into one incision wound. The retractor is formed of a tubular retractor main body holding an incision wound in an open state which is made by incising a body wall of a subject with a scalpel and a lid-like converter which closes an opening at an upper end of the retractor main body. A plurality of insertion holes (ports) for inserting treatment tools are formed in advance in the converter of PTL 1. In addition, PTL 2 discloses that a large number Of recesses are densely formed in a converter, or the converter is made into a planar plate.

By using a retractor, it is possible to perform less invasive surgery by decreasing an incision wound and to protect the incision wound from infection. In addition, the laparoscopic surgery is generally performed in a pneumoperitoneal manner in which the abdomen of a subject is expanded with pneumoperitoneum gas such as carbonic acid gas. The ports provided in the converter of PTL 1 have cross valves which are closed when the treatment tool is pulled out from the ports, and leakage of pneumoperitoneum gas is suppressed.

CITATION LIST

Patent Literature

[PTL 1] Japanese Unexamined Patent Application, First Publication No. 2002-28163
[PTL 2] Japanese Unexamined Patent Application, First Publication No. 2012-215

SUMMARY OF INVENTION

Technical Problem

Since the converter of PTL 1 has preliminarily formed several ports, the position at which the treatment tool can be inserted is specified. There is a problem in that the degree of freedom of a procedure is low since a practitioner cannot insert the treatment tool into any position. On the other hand, the converter of PTL 2 is an aggregate with many recesses or a planar plate, and therefore, a practitioner can form insertion holes (ports) by puncturing any positions with a trocar. However, since the converter of PTL 2 does not have a valve body, there is a problem that the pneumoperitoneum gas leaks when the trocar with which the converter is punctured is pulled out. For this reason, the converter of PTL 2 is restricted from re-sticking of the trocar. Moreover, in the converter thereof, it is necessary to precisely puncture a position corresponding to a target portion to be treated with the trocar and the degree of freedom of a procedure is impaired.

The present invention has been made from the viewpoint of the above-described problems, and provides a medical treatment implement which has an excellent degree of freedom of a procedure and into which a trocar can be re-stuck.

Solution to Problem

The present application includes the following aspects.

(1) A medical treatment implement including: a tubular retractor main body configured to be indwelled in an incision wound; and a converter configured to close an opening end portion of an upper end of the retractor main body and to be puncturable with a trocar, in which the converter includes: a ring-shaped frame portion detachably mounted on the opening end portion; and a sheet portion which is mounted inside the frame portion and airtightly covers the opening end portion, and a compression force is applied to the sheet portion in an inner diameter direction.

(2) The medical treatment implement according to (1), in which the sheet portion includes: a first layer on an upper surface side; and a second layer on a lower surface side close to the opening end portion, and the second layer has a tear strength higher than that of the first layer.

(3) The medical treatment implement according to (2), in which the first layer and the second layer are made of the same kinds of resin materials having different hardness and are fused to each other.

(4) The medical treatment implement according to (2) or (3), in which the second layer has a thickness dimension larger than that of the first layer.

(5) The medical treatment implement according to any one of (2) to (4), in which a reinforcing ring having a hardness higher than those of the first layer and the second layer is embedded between the first layer and the second layer.

(6) The medical treatment implement according to any one of (2) to (5), in which a protruding piece portion that protrudes in an inner diameter direction is formed in the frame portion along the inner periphery and is inserted with a pressure into a recess groove portion formed on a peripheral surface of the second layer.

Advantageous Effects of Invention

According to the medical treatment implement of the present invention, since the compression fierce is applied to the sheet portion of the converter in an inner diameter direction, when a trocar with which the sheet portion is punctured at any position is pulled out, the puncture hole is naturally closed by a compression force. For this reason, the puncture position on the sheet portion is not limited, the degree of freedom of a procedure becomes excellent, leakage of pneumoperitoneum gas is suppressed, and the re-sticking of the trocar is allowed.

DESCRIPTION OF EMBODIMENTS

Figure 1A:
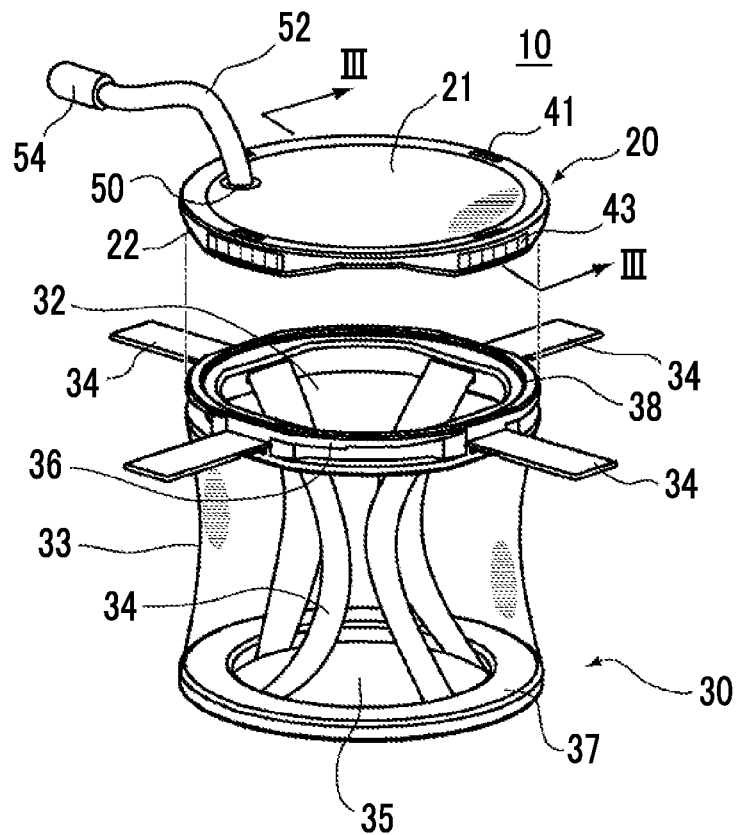
FIG. 1A is a perspective view showing a state in which a converter is separated from a retractor main body.

Hereinafter, an embodiment of the present invention will be described based on the drawings. In each drawing, the common reference numerals are given to corresponding constituent elements, and the detailed description thereof will not be repeated as appropriate. In the present specification, in order to describe the relative positional relationship between the converter and the retractor main body, the retractor main body side may be referred to as a lower side and the converter side may be referred to as an upper side in some cases. However, the vertical direction does not necessarily mean upper and lower portions in a gravity direction, and is not limited to an orientation of the medical treatment implement of the present invention when in use.

Figure 1B:
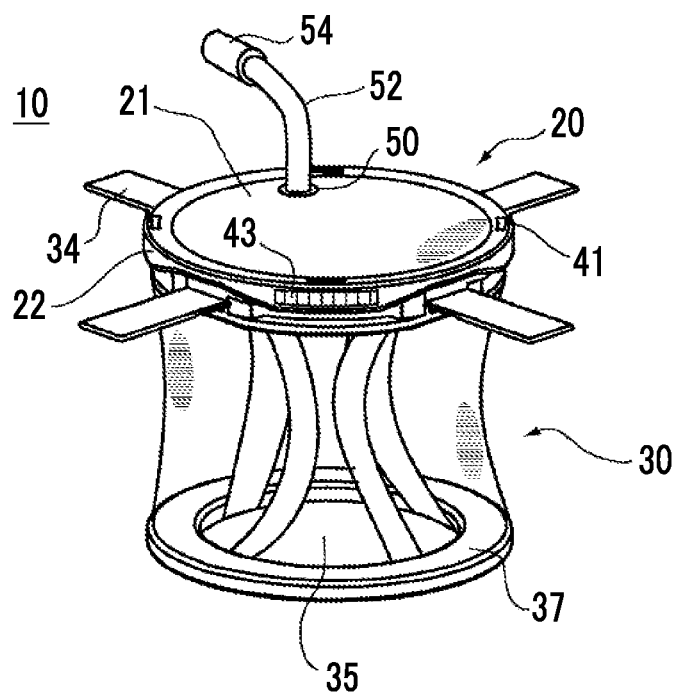
FIG. 1B is a perspective view showing a state in which the converter is mounted on the retractor main body.

FIGS. 1A and 1B are perspective views showing an example of a medical treatment implement 10 of the present embodiment. FIG. 1A shows a state in which a converter 20 is separated from a retractor main body 30, and FIG. 1B shows a state in which the converter 20 is mounted on the retractor main body 30.

Figure 2A:
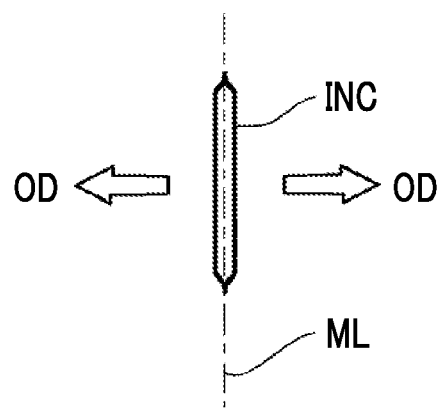
FIG. 2A is a plan view of an incision wound.
Figure 2B:
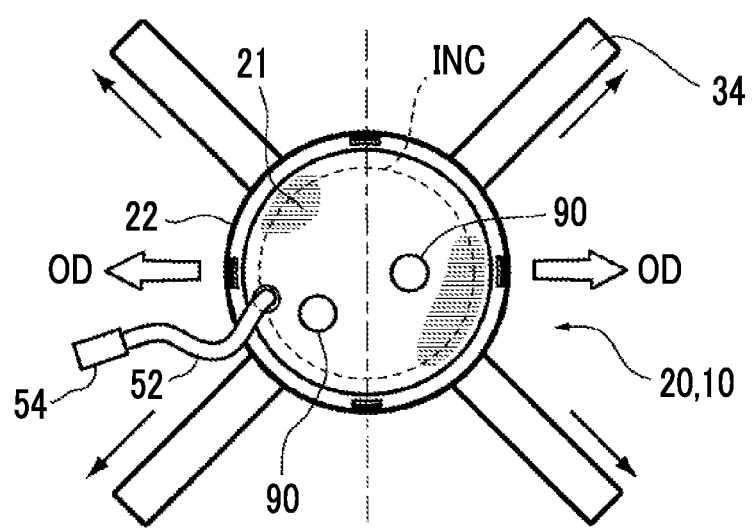
FIG. 2B is a plan view showing a state in which a medical treatment implement is indwelled in the incision wound to enlarge the incision wound.

2A and 2B are plan views showing a state in which the medical treatment implement 10 is indwelled in an incision wound INC. FIG. 2A is a plan view of the incision wound INC formed along a median line ML of the body surface such that the incision wound passes through the umbilicus of a subject. The opening direction OD in which the incision wound INC is enlarged by the medical treatment implement 10 is indicated by a void arrow in FIG. 2A. As shown in FIG. 2B, by pulling four tension belts 34 of the medical treatment implement 10 indwelled in the incision wound INC in a radial direction, the incision wound INC is enlarged in a substantially circular shape toward the opening direction OD (void arrow). In FIG. 2A, a case in which the straight line shaped incision wound INC is expanded in a substantially circular shape is exemplified, but the incision wound INC may have a cross shape. The cross-shaped incision wound INC is expanded in a square shape with four end points of the cross as apexes.

FIG. 2B shows a state in which the tension belts 34 are pulled in a state in which the converter 20 is mounted on the retractor main body 30 for explanation. However, the method of using the medical treatment implement 10 is not limited thereto. The retractor main body 30 alone may be indwelled in the incision wound INC without mounting the converter 20 thereon and the tension belts 34 may be pulled to enlarge the incision wound INC. On the other hand, the converter 20 may be mounted on the retractor main body 30 in states in which the sheet portion 21 of the converter 20 separated from the retractor main body 30 is punctured at desired positions with one or a plurality of trocars 90 (illustrated by circles in FIG. 2B) and the incision wound INC is sufficiently enlarged.

First, the summary of the present embodiment will be described.

The medical treatment implement 10 includes the tubular retractor main body 30 configured to be indwelled in the incision wound INC; and the converter 20 configured to close an opening end portion 32 of an upper end of the retractor main body 30 and to be puncturable with the trocar 90. The converter 20 includes a ring-shaped frame portion 22 detachably mounted on the opening end portion 32 and the sheet portion 21 which is mounted inside the frame portion 22 and airtightly covers the opening end portion 32. In the medical treatment implement 10 of the present embodiment, a compression force is applied to the sheet portion 21 in an inner diameter direction.

Next, the medical treatment implement 10 of the present embodiment will be described in detail. The medical treatment implement 10 of the present embodiment is a retractor and an instrument for maintaining and protecting the incision wound INC in an open state to support various treatments such as intraperitoneal observation, cleaning, excision, indwelling and recovery of instruments.

The retractor main body 30 is mounted on the incision wound INC so as to interpose the front and rear surfaces of the abdominal wall and is a member that applies a radially outward force to the incision wound INC to enlarge the incision wound. Although the specific structure of the retractor main body 30 is not particularly limited, the retractor main body includes, for example, a tubular member 33 having airtightness and flexibility, a first fixing member 37 and a second fixing member 38 with a cyclic flat plate shape which are provided on both ends of the tubular member 33.

The tubular member 33 of the present embodiment has a cylindrical shape and is made, for example, of resin materials such as a polyurethane resin, a soft vinyl chloride resin, a polyethylene resin, and a polypropylene resin.

The first fixing member 37 and the second fixing member 38 have a circular ring shape in plan view and are made, for example, of resin materials such as a vinyl chloride resin, an acrylonitrile-butadiene-styrene copolymer (ABS) resin, a polyamide resin, a polypropylene resin, a polyacetal resin, and polycarbonate resin.

The first fixing member 37 is a member constituting the opening end portion 35 at a lower end or the retractor main body 30 and is inserted into the abdominal cavity through the incision wound INC so as to be brought into close contact with the rear surface of the abdominal wall. The second fixing member 38 is a member constituting the opening end portion 32 at an upper end of the retractor main body 30 and is brought into close contact with the front surface (body surface) of the abdominal wall. A plurality of tension belts 34 extending over the first and second fixing members are provided in the retractor main body 30. The tension belts 34 are disposed so as to pass through the inside of the tubular member 33. Lower ends of the tension belts 34 are fixed to the first fixing member 37 and upper ends thereof are inserted into the second fixing member 38 from the radially inner side to the radially outer side. By pulling the upper ends of the tension belts 34 radially outward of the second fixing member 38, the first fixing member 37 is pulled up and the gap between the first fixing member and the second fixing member 38 is reduced. Accordingly, the first fixing member 37 and the second fixing member 38 are brought into close contact with the rear surface and the front surface of the abdominal wall, and the retractor main body 30 is indwelled in the incision wound INC. The opening end portion 32 at the upper end of the retractor main body 30 is formed on the front surface side of the incision wound INC. The opening end portion 32 is closed by detachably mounting the converter 20 on the second fixing member 38.

Figure 3:
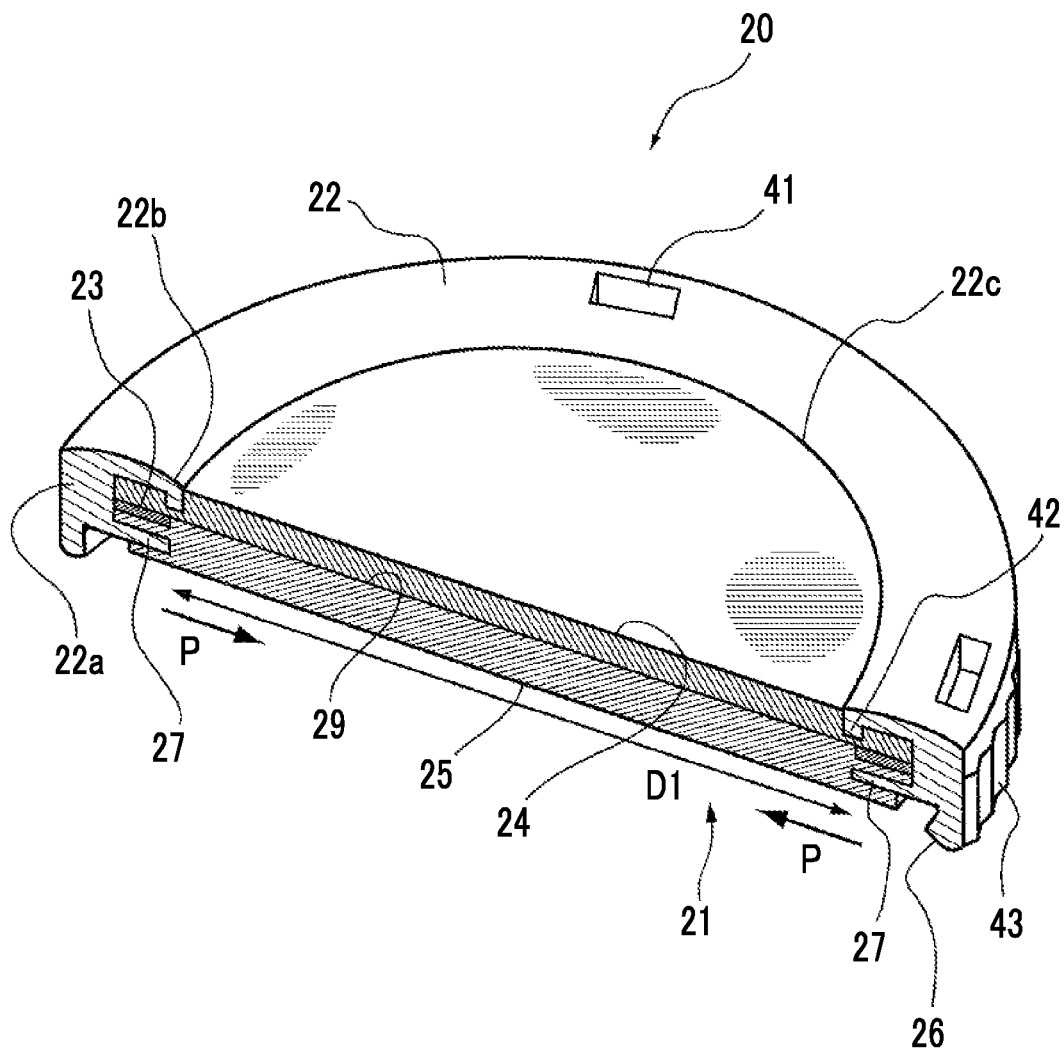
FIG. 3 is a cross-sectional view of the converter which is taken along line III-III of FIG. 1A.

FIG. 3 is a cross-sectional view of the converter 20 which is taken along line III-III of FIG. 1A. The converter 20 includes the sheet portion 21 and the frame portion 22. The sheet portion 21 is a member for air-tightly closing the opening end portion 32 on an upper end (proximal) side of the retractor main body 30. The frame portion 22 is a portion that is detachably mounted on the second fixing member 38 and has a ring shape. A predetermined number (four places at intervals of 90 degrees in the present embodiment) of engagement convex portions 26 are formed on an inner peripheral surface so as to protrude inward.

No port is previously formed in the sheet portion 21 except for an air supply port 50. A practitioner can puncture the sheet portion 21 at any position in the vicinity of the center of the sheet portion with the trocar 90 and can insert various treatment tools into a lumen of the trocar 90 to use these for a procedure. A trocar 90 having an outer diameter of, for example, 5 mm to 12 mm can be used. Examples of the treatment tools include an optical scope such as a charge coupled device (CCD) camera, a forceps for gripping, an electric scalpel or an ultrasonic scalpel for excision, a scissor forceps, a stapler, a thread and a needle, gauze, a clip device, a collection bag, a suction tube, or a trocar (cannula) configured to allow insertion of these materials, but are not limited thereto.

In laparoscopic surgery, another trocar with which the body wall is punctured may be used in combination without using the medical treatment implement 10 in addition to the trocar 90 with which the medical treatment implement 10 is punctured.

A locking portion 36 engaging with the engagement convex portion 26 is provided around the cyclic second fixing member 38 of the retractor main body 30 at positions and quantities corresponding to the engagement convex portion 26. By screwing the converter 20 with respect to the retractor main body 30 in a right-screw direction (clockwise when the converter 20 is viewed from above), the engagement convex portion 26 abuts on the locking portion 36 and is locked. On the other hand, when the converter 20 is rotated around a shaft with respect to the retractor main body 30 in an opposite direction (counterclockwise), the engagement convex portion 26 is separated from the locking portion 36 and the engagement therebetween is released. Therefore, the converter 20 can be separated from the retractor main body 30. A linger-hook projection 43 and an index hole 41 are formed on an outer peripheral surface of a place of the frame portion 22 where the engagement convex portion 26 is formed. By screwing the converter 20 with respect to the retractor main body 30 in the right-screw direction in a state in which the index hole 41 is aligned with the tension belts 34, the engagement convex portion 26 is engaged with the locking portion 36 and is locked. Accordingly, a practitioner can easily mount the converter 20 on the retractor main body 30 using the index hole 41 as a mark.

Another index portion using a printed symbol or the like may be provided in the frame portion 22 instead of or in addition to the index hole 41.

As shown in FIGS. 1A and 1B, the air supply port 50 for supplying pneumoperitoneum gas into a body cavity is formed in the sheet portion 21, and the connector 54 and the air supply port 50 communicate with each other via an air supply tube 52. A device for supplying pneumoperitoneum gas such as carbonic acid gas is mounted in the connector 54. Pneumoperitoneum gas is supplied from the air supply port 50 into a body cavity through the interior of the retractor main body 30 during a procedure of laparoscopic surgery.

Figure 4:
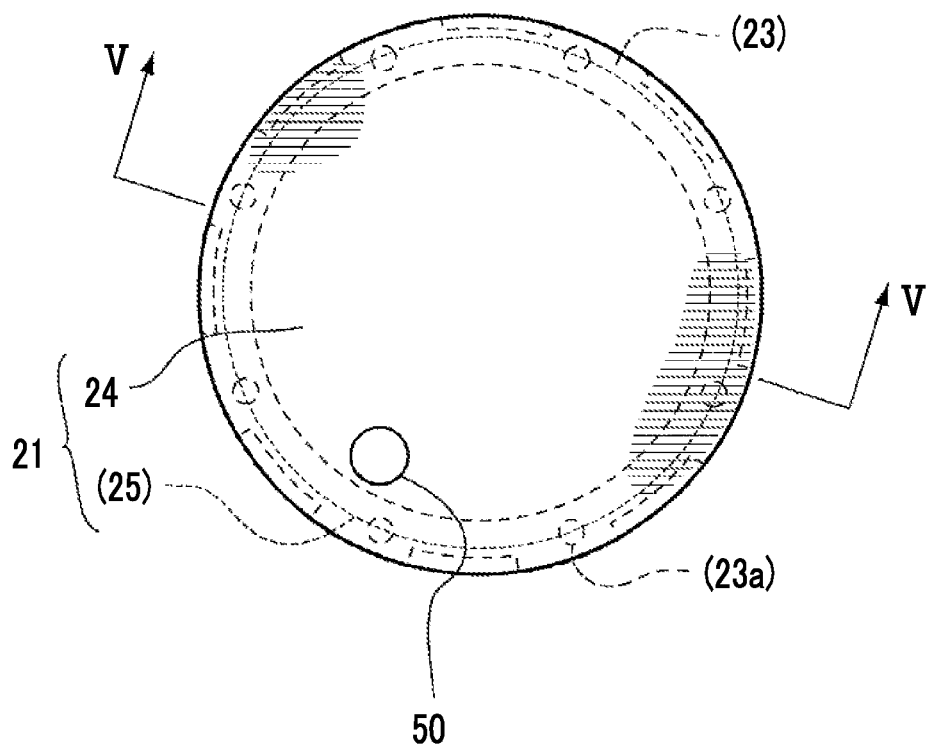
FIG. 4 is a plan view of a sheet portion.
Figure 5:
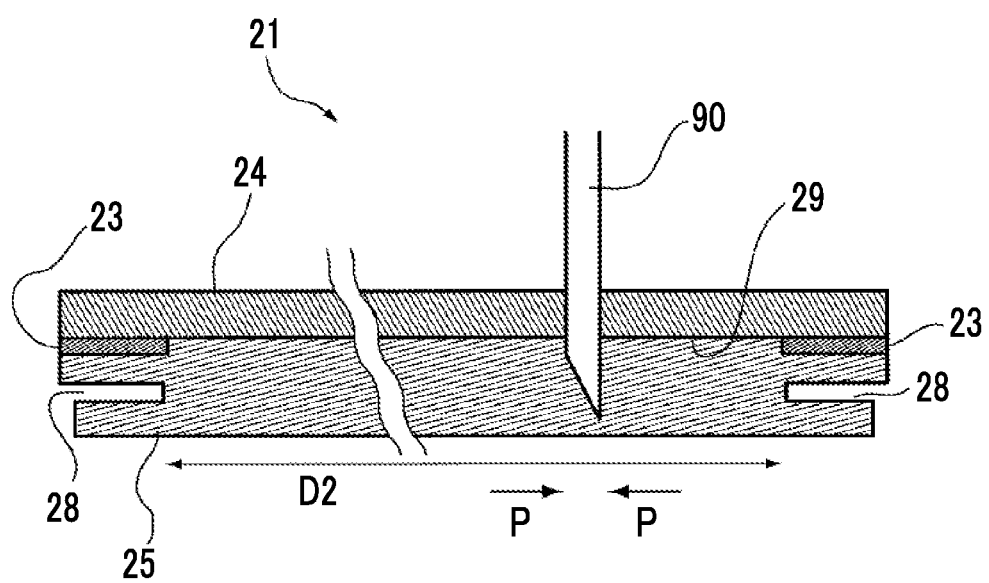
FIG. 5 is a cross-sectional view taken along line V-V of FIG. 4.

FIG. 4 is a plan view of the sheet portion 21. FIG. 5 is a cross-sectional view taken along line V-V of FIG. 4. The converter 20 of the present embodiment will be described in more detail with reference to FIGS. 3 to 5.

The frame portion 22 has a circular ring shape in plan view. The frame portion 22 can be made of hard resins such as a vinyl chloride resin, an acrylonitrile-butadiene-styrene copolymer (ABS) resin, a polyamide resin, a polyethylene resin, a polypropylene resin, a polyacetal resin, polycarbonate resin, and a polysulfone resin. Here, "hard" means that the durometer A hardness based on JIS K6253 is high (for example, 10 degrees to 60 degrees).

The frame portion 22 has an F-shaped cross section. As shown in FIG. 3, the frame portion 22 includes a side peripheral portion 22a, an upper ring portion 22b protruding in an cave shape from an upper portion of the side peripheral portion 22a to an inner diameter side, and a protruding piece portion 27 which is below the upper ring portion 22b and protrudes in a flange shape from the side peripheral portion 22a to the inner diameter side. A claw portion 42 is formed on a lower surface side of the upper ring portion 22b so as to protrude downward. The engagement convex portions 26 are protrusively formed on an inner diameter side at a lower end of the side peripheral portion 22a while being spaced at 4 places of the frame portion 22 in a circumferential direction. The protruding piece portion 27 is formed substantially parallel to the upper ring portion 22b. In the present embodiment, the side peripheral portion 22a and the protruding piece portion 27 are integrally made of one material. However, instead of this, the upper ring portion 22b and the protruding piece portion 27 may be integrally produced using members different from each other.

The sheet portion 21 is made of a soft resin material that can be punctured with the trocar 90. The sheet portion 21 may be formed of a single layer. However, the sheet portion is formed of multiple layers in the present embodiment. Accordingly, it is possible to achieve both easiness of puncturing using the trocar 90 and prevention of leakage of pneumoperitoneum gas. The sheet portion 21 is mounted below and inside the frame portion 22.

The sheet portion 21 of the present embodiment includes a first layer 24 on an upper surface side and a second layer 25 on a lower surface side close to the opening end portion 32. The second layer 25 is made of a resin material having a tear strength higher than that of the first layer 24. The sheet portion 21 may be formed of three or more layers.

The sheet portion 21 is a flat, film-shaped member having flexibility. An index portion not shown in the drawing may be displayed on the surface of the sheet portion 21. The sheet portion 21 can be made of soft resin materials such as a hydrogenated styrene-based thermoplastic elastomer (SEBS) resin, silicone rubber, natural rubber, or a polyurethane resin. For example, the first layer 24 can be made of SEBS having a low durometer. A hardness based on JIS K6253 (10 degrees to 40 degrees), and the second layer 25 can be made of SEBS having a high durometer A hardness (25 degrees to 60 degrees). In this case, the tear strength of the first layer 24 is 5 [kN/m] to 10 [kN/m], the tear strength of the second layer 25 is 10 [kN/m] to 20 [kN/m] which is greater than that of the first layer 24. In a case where the tear strength of the first layer 24 is greater than or equal to 5 [kN/m], unexpected formation of perforations due to the trocar 90 coming into contact with the first layer 24 can be reduced. In a case where the tear strength thereof is less than or equal to 10 [kN/m], it is possible to start puncturing of the sheet portion 21 with the trocar 90 without applying an excessive force to the sheet portion. In addition, in a case where the tear strength of the second layer 25 is greater than or equal to 10 [kN/m], a puncture hole when the trocar 90 is removed from the second layer 25 is favorably closed. In a case where the tear strength thereof is less than or equal to 20 [kN/m], there is no excessive drag caused when the second layer 25 is continuously punctured with the trocar 90 penetrating the first layer 24. The tear strength can be measured through a method prescribed in JIS K6252.

By forming the first layer 24 on the upper surface side with a resin material having a low durometer A hardness and a low tear strength, the sheet portion 21 is easily punctured with the trocar 90. On the other hand, by forming the second layer 25 on the lower surface side facing the opening end portion 32 (refer to each drawing in FIG. 1) of the retractor main body 30 with a resin material having a high durometer A hardness and a high tear strength, the second layer 25 is not split even if the trocar 90 is stuck, and a puncture hole of the trocar 90 is airtightly closed by a compression force applied to the sheet portion 21 when the trocar 90 is removed.

The upper ring portion 22b and the protruding piece portion 27 interpose a part of the sheet portion 21 therebetween, and the upper ring portion prevents the sheet portion 21 from falling off from an opening inner edge 22c of the frame portion 22 upward. The claw portion 42 is formed on the lower surface side of the upper ring portion 22b, more specifically, below the opening inner edge 22c. The claw portion 42 bites into the surface of the sheet portion 21 and further suppresses the sheet portion 21 from falling off from the opening inner edge 22c of the frame portion 22 upward.

The protruding piece portion 27 is a portion which is inserted into a recess groove portion 28 (refer to FIGS. 4 and 5) of the sheet portion 21 to apply a compression force P to the sheet portion 21 in an inner diameter direction, that is, in an in-plane direction of the sheet portion 21. The recess groove portions 28 are formed in a plurality of places on a side peripheral surface of the sheet portion 21 (specifically, the second layer 25). The recess groove portions 28 define the inner diameter direction of the sheet portion 21 as a depth direction. In the present embodiment, the recess groove portions 28 are formed in eight places around the sheet portion 21, and the protruding piece portions 27 are formed in the frame portion 22 at positions and quantities corresponding to the recess groove portions 28. The number of recess groove portions 28 and protruding piece portions 27 is not limited to the above.

In a state where the sheet portion 21 is separated from the frame portion 22, a diameter D1 (refer to FIG. 3) of an imaginary circle drawn by protruding ends of the protruding piece portions 27 protruding in a plurality of places on the inner peripheral side of the frame portion 22 is smaller than a diameter D2 (refer to FIG. 5) of an imaginary circle drawn by bottom portions of the recess groove portions 28. The sheet portion 21 is mounted by being forcedly fitted on the lower surface side of the frame portion 22 in a state in which the protruding piece portions 27 are inserted into the recess groove portions 28. Specifically, it is preferable that the above-described diameter D2 is larger than the diameter D1 within a range of 5% to 20%.

That is, the protruding piece portions 27 that protrude in the inner diameter direction are formed in the frame portion 22 along the inner periphery and are inserted with a pressure into the recess groove portions 28 formed on the peripheral surface of the sheet portion 21 (specifically, the second layer 25). Accordingly, a compression force P is applied to the sheet portion 21 in the inner diameter direction. By compressing the recess groove portions 28 in the inner diameter directions of the protruding piece portions 27, the second layer 25 of the sheet portion 21 are held in the frame portion 22 in a contracted state in the radial direction. Accordingly, the compression force P is generated at all times in the second layer 25 radially inward as shown in FIGS. 3 and 5. Therefore, in a case where the trocar 90 is pulled out, the puncture hole is airtightly closed.

It is preferable that the first layer 24 and the second layer 25 are made of the same kinds of resin materials having different hardness (durometer A hardness) and are fused to each other. That is, the resin materials are mutually melted and integrally fixed to each other in a fusion interface 29 between the first layer 24 and the second layer 25. The same kinds of resin materials refer to resin materials having the same chemical structural form. In a case where the first layer 24 and the second layer 25 are made of the same kinds of resin materials, the compatibility between the first layer 24 and the second layer 25 is improved. In a case where the first layer 24 is made of SEBS with a low durometer A hardness (10 degrees to 40 degrees) and the second layer 25 is made of SEBS with a high durometer A hardness (25 degrees to 60 degrees), the durometer A hardness of the first layer 24 is 10 to 15 and the durometer A hardness of the second layer 25 is 25 to 35. In a case where the durometer A hardness of the first layer 24 is within the above-described range, it is possible to start puncturing of the sheet portion 21 with the trocar 90 without applying an excessive force to the sheet portion. In addition, in a case where the durometer A hardness of the second layer 25 is within the above-described range, there is no excessive drag caused when the second layer 25 is continuously punctured with the trocar 90 penetrating the first layer 24 while obtaining sufficient airtightness. The durometer A hardness of the first layer 24 and the second layer 25 can be measured through a method prescribed in JIS K6253.

Since the first layer 24 and the second layer 25 are mutually melted, even if the compression force P is applied to the second layer 25 from the protruding piece portions 27 in the inner diameter direction, the fusion interface 29 is prevented from peeling off. In addition, the drag received by the trocar 90 with which the first layer 24 is punctured and which is deeply pushed into the first layer does not increase discontinuously at the fusion interface 29. For this reason, the trocar 90 with which the first layer 24 is punctured can be pushed into the second layer 25 through the fusion interface 29 to penetrate through the second layer 25.

The thickness dimensions of the first layer 24 and the second layer 25 are not particularly limited, but it is preferable that the thickness dimension of the second layer 25 is larger than that of the first layer 24. Accordingly, the puncture hole generated in the second layer 25 by the trocar 90 can be closed again with high airtightness. Specifically, in a case where the thickness dimension of the first layer 24 is 1, the thickness dimension of the second layer 25 is preferably 1.2 to 5 and more preferably 1.5 to 3.

As shown in FIGS. 3 to 5, a reinforcing ring 23 is embedded between the first layer 24 and the second layer 25. The reinforcing ring 23 is preferably made of a resin material harder than those of the first layer 24 and the second layer 25. That is, the durometer A hardness of the reinforcing ring 23 based on JIS K6253 is preferably higher than that of the first layer 24 and the second layer 25 based on JIS K6253. Similarly to the frame portion 22, the reinforcing ring 23 can be made of hard resins such as a vinyl chloride resin, an acrylonitrile-butadiene-styrene copolymer (ABS) resin, a polyamide resin, a polyethylene resin, a polypropylene resin, a polyacetal resin, polycarbonate resin, and a polysulfone resin.

In a case of manufacturing the sheet portion 21, the reinforcing ring 23 may be previously molded, the reinforcing ring 23 may be disposed in a mold, the first layer 24 may be insert-molded on the upper surface side of the reinforcing ring 23, and the second layer 25 may be further insert-molded on the lower surface side of the reinforcing ring 23 while changing the mold. At the time of insert-molding of the second layer 25 having a high durometer A hardness and a high melting point, the first layer 24 having a low durometer A hardness and a low melting point is heated and melted, to form the fusion interface 29 at the joint portion of the first layer 24 and the second layer 25.

As shown in FIG. 4, a thick-width portion and a thin-width portion are alternately repeatedly formed in the reinforcing ring 23 and a through-hole 23a is formed in the thick-width portion. A plurality of through-holes 23a are formed in the reinforcing ring 23 apart from each other in the circumferential direction, The first layer 24 is formed in a circular shape having the same diameter as that of the thick width portion and covers the entire reinforcing ring 23. As shown in FIG. 5, the second layer 25 is stacked on the lower surface side of the reinforcing ring 23. At the time of insert-molding of the first layer 24 or the second layer 25, each of the resin materials flows into the through-holes 23a to join both layers. Accordingly, the reinforcing ring 23 is favorably anchored to the first layer 24 and the second layer 25.

In the case where the sheet portion 21 includes the reinforcing ring 23 harder than the first layer 24 or the second layer 25, the sheet portion 21 is prevented from falling off from the frame portion 22. That is, since the cyclic reinforcing ring 23 is embedded in the sheet portion 21, deformation of the sheet portion 21 can be suppressed. Particularly, since the reinforcing ring 23 is joined to the first layer 24, deformation of the first layer 24 is favorably suppressed by the stiffness of the reinforcing ring 23.

In the converter 20 described above, since the tear strength of the first layer 24 on the upper surface side is relatively low, it is possible to easily start the puncturing with the trocar 90. Since the first layer 24 and the second layer 25 are integrated through fusion, the trocar 90 can also be pushed into the second layer 25 having a high resin hardness or tear strength. Since the compression force P is applied to the second layer 25 in the inner diameter direction., the puncture hole generated when the trocar 90 is re-stuck is immediately closed by the compression force P, so that the converter 20 can maintain the airtightness.

The quality of the airtightness of the converter 20 can be confirmed by, for example, the following leakage test That is, in a case where pneumoperitoneum gas is supplied into a body cavity through the air supply port 50 at a flow rate of 5 liters per minute, whether or not a desired internal pressure (for example, greater than or equal to 1.2 kPa) is maintained in the body cavity may be measured. In the converter 20 of the present embodiment, an internal pressure of greater than or equal to 2 kPa was confirmed through the above-described leakage test under the condition that the sheet portion 21 was once punctured with two trocars having an outer diameter of 7 mm and was allowed to stand over 2 hours or longer, and then, the trocars were removed.

From this, it can be said that the medical treatment implement 10 of the present embodiment has an excellent degree of freedom of a procedure since leakage of pneumoperitoneum gas is prevented by applying the compression force P to the sheet portion 21 in the inner diameter direction even if the trocars are re-stuck at any timing during a long-time procedure.

The present invention is not limited to the above-described embodiment, but includes aspects such as various modifications and improvements as long as the object of the present invention is achieved.

For example, the specific structure of the retractor main body 30 is not particularly limited, and it is optional to provide the tension belts 34.

A circular recess groove to which the claw portion 42 of the frame portion 22 is fitted may be formed on the upper surface of the first layer 24.

INDUSTRIAL APPLICABILITY

According to the medical treatment implement of the present invention, since the compression force is applied to the sheet portion of the converter in an inner diameter direction, when a trocar with which the sheet portion is punctured at any position is pulled out, the puncture hole is naturally closed by a compression force. For this reason, the puncture position on the sheet portion is not limited, the degree of freedom of a procedure becomes excellent, leakage of pneumoperitoneum gas is suppressed, and the re-sticking of the trocar is allowed.

REFERENCE SIGNS LIST 10 medical treatment implement
20 converter
21 sheet portion
22 frame portion
22a side peripheral portion
22b upper ring portion
22c opening inner edge
23 reinforcing ring
23a through-hole
24 first layer
25 second layer
26 engagement convex portion
27 protruding piece portion
28 recess groove portion
29 fusion interface
30 retractor main body
32 opening end portion
33 tubular member
34 tension belt
35 opening end portion
36 locking portion
37 first fixing member
38 second fixing member
41 index hole
42 claw portion
43 finger-hook projection
50 air supply port
52 air supply tube
54 connector
90 trocar

The invention claimed is:
1. A medical retractor device, comprising:
a retractor main body having a tubular shape and configured to be indwelled in an incision wound; and a converter configured to close an opening at an upper end of the retractor main body and to be punctured with a trocar, wherein the converter comprises a frame portion detachably mounted on the upper end of the retractor main body and having a ring shape, a sheet portion mounted to the frame portion and comprising a first layer and a second layer having a tear strength higher than a tear strength of the first layer, and a reinforcing ring embedded between the first and second layers of the sheet portion and having a plurality of through-holes in which the first layer facing an outer side of the retractor main body and the second layer facing an inner side of the retractor main body are joined, and the converter is configured such that the sheet portion forms an air-tight covering of the opening at the upper end of the retractor main body, and wherein the reinforcing ring has a hardness that is higher than a hardness of the first layer and a hardness of the second layer and wherein a compression force is applied to the sheet portion radially inward of the opening in a direction along an inner diameter of the sheet portion.

2. The medical retractor device according to claim 1, wherein the first layer and the second layer are made of resin materials such that the resin material of the first layer and the resin material of the second layer have a same chemical structural form and different hardness and are fused to each other.

3. The medical retractor device according to claim 2, wherein the second layer has a thickness that is larger than a thickness of the first layer.

4. The medical retractor device according to claim 2, wherein the second layer of the sheet portion has a groove portion formed on a peripheral surface of the second layer, and the frame portion of the converter has a protruding piece portion protruding radially inward of the frame portion in a direction along an inner diameter of the sheet portion and formed along an inner periphery of the frame portion such that the protruding piece portion is inserted with a pressure into the groove portion of the second layer.

5. The medical retractor device according to claim 1, wherein the second layer has a thickness that is larger than a thickness of the first layer.

6. The medical retractor device according to claim 5, wherein the second layer of the sheet portion has a groove portion formed on a peripheral surface of the second layer, and the frame portion of the converter has a protruding piece portion protruding radially inward of the frame portion in a direction along an inner diameter of the sheet portion and formed along an inner periphery of the frame portion such that the protruding piece portion is inserted with a pressure into the groove portion of the second layer.

7. The medical retractor device according to claim 1, wherein the second layer of the sheet portion has a groove portion formed on a peripheral surface of the second layer, and the frame portion of the converter has a protruding piece portion protruding radially inward of the frame portion in a direction along an inner diameter of the sheet portion and formed along an inner periphery of the frame portion such that the protruding piece portion is inserted with a pressure into the groove portion of the second layer.

8. The medical retractor device according to claim 1, wherein each of the first layer and the second layer comprises a resin material, and the converter is formed such that the resin materials of the first and second layers are fused in the plurality of through-holes in the reinforcing ring.

9. The medical retractor device according to claim 1, wherein the reinforcing ring comprises a resin material, each of the first layer and the second layer comprises a resin material, and the converter is formed such that the resin materials of the first and second layers are fused in the plurality of through-holes in the reinforcing ring.

10. The medical retractor device according to claim 1, wherein the frame portion of the converter has a claw portion protruding into the first layer of the sheet portion from an upper surface of the first layer, and a protruding piece portion protruding into the second layer of the sheet portion in a direction along an inner diameter of the sheet portion such that the protruding piece portion applies a compression force to the sheet portion.

11. The medical retractor device according to claim 1, wherein the sheet portion of the converter is formed such that the tear strength of the first layer is in a range of 5 to 10 kN/m and that the tear strength of the second layer is in a range of 10 to 20 kN/m.

12. The medical retractor device according to claim 1, wherein the sheet portion of the converter is formed such that the first layer has a durometer A hardness in a range of 10 to 40 degrees and that the second layer has a durometer A hardness in a range of 25 to 60 degrees.

13. The medical retractor device according to claim 12, wherein the converter is formed such that the reinforcing ring has a durometer A hardness that is higher than the durometer A hardness of the first layer and the durometer A hardness of the second layer.

14. The medical retractor device according to claim 1, wherein the sheet portion of the converter is formed such that the second layer has a durometer A hardness that is higher than a durometer A hardness of the first layer.

15. The medical retractor device according to claim 14, wherein the sheet portion of the converter is formed such that the durometer A hardness of the first layer is in a range of 10 to 15 degrees and that the durometer A hardness of the second layer is in a range of 25 to 35 degrees.

16. The medical retractor device according to claim 1, wherein the converter is formed such that the reinforcing ring has a durometer A hardness that is higher than a durometer A hardness of the first layer and a durometer A hardness of the second layer.

17. The medical retractor device according to claim 1, wherein the sheet portion is formed such that the first layer comprises a resin material selected from the group consisting of a hydrogenated styrene-based thermoplastic elastomer resin, silicone rubber, natural rubber and a polyurethane resin and that the second layer comprises a resin material selected from the group consisting of a hydrogenated styrene-based thermoplastic elastomer resin, silicone rubber, natural rubber and a polyurethane resin.

18. The medical retractor device according to claim 1, wherein each of the first layer and the second layer comprises a resin material selected from the group consisting of a hydrogenated styrene-based thermoplastic elastomer resin, silicone rubber, natural rubber and a polyurethane resin such that the resin material of the first layer and the resin material of the second layer have a same resin material and different hardness.

19. The medical retractor device according to claim 1, wherein the converter is formed such that the reinforcing ring comprises a resin material selected from the group consisting of a vinyl chloride resin, an acrylonitrile-butadiene-styrene copolymer resin, a polyamide resin, a polyethylene resin, a polypropylene resin, a polyacetal resin, a polycarbonate resin and a polysulfone resin, and that the frame portion comprises a resin material selected from the group consisting of a vinyl chloride resin, an acrylonitrile-butadiene-styrene copolymer resin, a polyamide resin, a polyethylene resin, a polypropylene resin, a polyacetal resin, a polycarbonate resin and a polysulfone resin.

20. The medical retractor device according to claim 1, wherein the reinforcing ring comprises a resin material selected from the group consisting of a vinyl chloride resin, an acrylonitrile-butadiene-styrene copolymer resin, a polyamide resin, a polyethylene resin, a polypropylene resin, a polyacetal resin, a polycarbonate resin and a polysulfone resin, and the sheet portion is formed such that the first layer comprises a resin material selected from the group consisting of a hydrogenated styrene-based thermoplastic elastomer resin, silicone rubber, natural rubber and a polyurethane resin and that the second layer comprises a resin material selected from the group consisting of a hydrogenated styrene-based thermoplastic elastomer resin, silicone rubber, natural rubber and a polyurethane resin.

* * * * *